US005455039A

United States Patent [19]
Edelman et al.

[11] Patent Number: 5,455,039
[45] Date of Patent: Oct. 3, 1995

[54] EXTRALUMINAL REGULATION OF THE GROWTH AND REPAIR OF TUBULAR STRUCTURES IN VIVO

[75] Inventors: Elazer R. Edelman, Brookline; David H. Adams, Boston; Morris J. Karnovsky, Newton Centre, all of Mass.

[73] Assignee: President and Fellows of Harvard College, Cambridge, Mass.

[21] Appl. No.: 225,429

[22] Filed: Apr. 8, 1994

Related U.S. Application Data

[63] Continuation of Ser. No. 769,162, Sep. 27, 1991, abandoned, which is a continuation of Ser. No. 436,337, Nov. 13, 1989, abandoned.

[51] Int. Cl.$^6$ ..................................................... A61K 9/12
[52] U.S. Cl. ........................... 424/422; 424/423; 424/426
[58] Field of Search ...................................... 424/422, 423, 424/426; 514/56, 423, 12

[56] References Cited

U.S. PATENT DOCUMENTS

| | | | |
|---|---|---|---|
| 3,797,485 | 3/1974 | Urguhart | 424/422 |
| 3,993,071 | 11/1976 | Higuchi et al. | 128/260 |
| 4,391,797 | 7/1983 | Folkman et al. | 424/19 |
| 4,495,174 | 1/1985 | Allock et al. | 424/78 |
| 4,808,402 | 2/1989 | Leibovich | 424/423 |
| 4,898,732 | 2/1990 | Fernandez | 424/422 |

OTHER PUBLICATIONS

Mayberg et al., 1988, Surgical Forum 39:496–499.
Okada et al., 1988, 19:1470–1476.
Okada et al., 1989 Neurosurgery 25:892–898.
Lotran et al., 1989 Robbins Pathologic Basis of Disease, pp. 73–74, 253–254, 553–557, 562–565.
Mayberg et al. 1981, Science 213:228–230.
Moskowitz et al., 1981, Brain Research 212:460–465.
Anti coagulant, anti thrombotic and thrombolytic drugs O'Reilly in The Phamacologic Basics of Therapeutics, 7th ed. Gilman et al eds. McMillan Pub. Co. 1985, p. 1338.
Inhibitors of angiotensin–converting enzyme prevent myointimal proliferate powell et al. Science 245, 186 (1989).
Structural Determinants of the Capacity of Heparin to Inhibit the Proliferate—Costellot et al. J. Cell Physiol. 120, 315 (1984).
Considerazioni sull'uso dell— Molino et al. Min. Cardioang., 21, 553 (1973).
Powell et al. Science 245, 186 (1989).
Costellot et al J. Cell Physiol. 120, 315 (1984).
Molino et al. Min. Cardioang. 21, 553 (1973).
Okada et al, Neurosurgery, 25, 892, 1989.
Okada et al, Stroke 19, 1470, 1988.
McBride, et al., "Restenosis After Successful Coronary Angioplasty: Pathophysiology and Prevention," The New England Journal of Medicine, vol. 318, No. 26: 1734–1737 (1988).
Simpfendorfer, "Acute Coronary Occlusion After Percutaneous Transluminal Coronary Angioplasty," Cleveland Clinic Journal of Medicine, vol. 55, No. 5: 429–432 (1988).
Fishman, et al., "Endothelial Regeneration in the Rat Cartoid Artery and the Significance of Endothelial Denudation in the Pathogenesis of Myointimal Thickening," Laboratory Investigation, vol. 32, No. 3: 339–351 (1975).
Austin, et al. "Intimal Proliferation of Smooth Muscle Cells as an Explanation for Recurrent Coronary Artery Stenosis After Percutaneous Transluminal Coronary Angioplasty," J. Am. Coll. Cardiol., vol. 6, No. 2: 369–375 (1985).
Diaz–Flores, et al., "Relation Between Arterial Intimal Thickening and the Vasa–Vasorum," Virchows Arch [Pathol Anat], vol. 406: 165–177 (1985).
Steele, et al., "Balloon Angioplasty: Natural History of the Pathophysiological Response to Injury in a Pig Model," Circulation Research, vol. 57, No. 1: 105–112 (1985).
Clowes, et al., "Suppression by Heparin of Smooth Muscle Cell Proliferation in Injured Arteries," Nature, vol. 265:625–626 (1977).
Castellot, Jr., "Structural Determinants of the Capacity of Heparin to Inhibit the Proliferation of Vascular Smooth Muscle Cells," Journal of Cellular Physiology, vol. 120:315–320 (1984).
Castellot, Jr., et al., "Structural Determinants of the Capacity of Heparin to Inhibit the Proliferation of Vascular Smooth Muscle Cells. II".
"Evidence for a Pentasaccharide Sequence That Contains a 3–O–Sulfate Group," The Journal of Cell Biology, vol. 102:1979–1984 (1986).
Jaques, "Drug Prophylaxis in Atherosclerosis," Artery, vol. 14, No. 4:209–215 (1987).
Bick, et al., "Clinical Use of Intrapulmonary Heparin," Seminars in Thrombosis and Hemostasis, vol. 11, No. 2:213–217 (1985).
Mahadoo, et al., "Cellular Control of Heparin in Blood," Medical Hypotheses 5:825–841 (1979).
Mahadoo, et al., "Endothelial Sequestration of Heparin Administered by the Intrapulmonary Route," Artery, vol. 7, No. 5:438–477 (1980).
Larsen, et al., "Oral Heparin Results in the Appearance of Heparin Fragments in the Plasma of Rats," Proc. Natl. Acad. Sci. USA, vol. 83: 2964–2968 (1986).
Bentley, et al., "An Objective Study of Alternative Methods of Heparin Administration," Thrombosis Research, vol. 18:177–187 (1980).
Dawes, et al., "Absorption of Heparin, LMW Heparin and SP54 After Subcutaneous Injection, Assessed by Competitive Binding Assay," Thrombosis Research, vol. 44:683–693 (1986).
Habib, et al., "Preservation of Endothelium–Dependent Vascular Relaxation in Cholesterol–Fed Rabbit by Treatment (List continued on next page.)

*Primary Examiner*—Gollamudi S. Kishore
*Attorney, Agent, or Firm*—Fish & Richardson

[57] ABSTRACT

A method of regulating repair in a physiological system following injury to the lumen of a tubular structure in that system, and of testing the effectiveness of regulatory agent, is presented. The method includes administering a modulator of cell or tissue growth to an extraluminal site adjacent the injured tissue.

10 Claims, No Drawings

OTHER PUBLICATIONS with the Calcium Blocker PN 200110," Circulation Research, vol. 58, No. 2:305–309 (1986).

Whitworth, et al., "Effect of Nifedipine on Recurrent Stenosis After Percutaneous Transluminal Coronary Angioplasty," J. Am. Coll. Cardiol., vol. 8:1271–1276 (1986).

Powell et al., "Inhibitors of Angiotensin–Converting Enzyme Prevent Myointimal Proliferation After Vascular Injury," Science, vol. 245:186–188 (1989).

Gordon et al., "Clinical Cardiology: Restenosis After PTCA," Circ. Supp. Abstracts of the 60th Scientific Sessions, vol. 76, No. 4: IV–213 (1987).

Langer et al., "Controlled Release and Magnetically Modulated Release Systems for Macromolecules," Methods in Enyzmology, 112:399–423 (1985).

Brown, et al., "In Vivo and In Vitro Release of Macromolecules from Polymeric Drug Delivery Systems," Journal of Pharmaceutical Sciences, vol. 72, No.10:1181–1185 (1983).

Sparer, et al., "Controlled Release From Erodible Poly(ortho Ester) Drug Delivery Systems," Journal of Controlled Release, vol. 1:23–32 (1984).

Lawter, et al., "Drug Release From Poly(Glycolide–CO–DL–Lactide) Microcapsules," Proceed. Intern. Symp. Control Rel. Bioact. Mater., vol. 14:99–100 (1987).

Neenan, et al., "Synthesis of a Heparinized Poly(Organophosphazene)," Biomaterials, vol. 3:78–80 (1982).

Grolleman, et al., "Studies on a Bioerodible Drug Carrier System Based on Polyohosphazene Part I. Synthesis," Journal of Controlled Release, vol. 3:143–154 (1986).

Ellis et al., "Results of a Randomized Trial of Heparin and Aspirin vs. Aspirin Alone for Prevention of Accute Closure and Restenosis After Angioplasty," Circ. Supp. Abstracts of the 60th Scientific Sessions, vol. 76, No. 4:IV–213 (1987).

Langer et al., "Controlled Release and Magnetically Modulated Systems for Macromolecular Drugs," Annals New York Academy of Sciences, 446:1–13 (198?).

Stemerman et al., "Experimental Arteriosclerosis," The J. of Experimental Medicine, 136:769–789 (1972).

Guyton et al., "Smooth Muscle Cell Proliferation in the Occluded Rat Carotid Artery," American J. of Path., 94:585–596 (1979).

Castellot, Jr. et al., "Cultured Endothelial Cells Produce a Heparinlike Inhibitor of Smooth Muscle Cell Growth," J. of Cell Bio., 90:372–379 (1981).

Molino et al., "Considerazioni sull'uso dell'Eparina long–term nei cardiovasculopatici," Min. Cardioang., 21:553–557 (1973).

O'Reilly, "Anticoagulant, Antithrombotic, and Thrombolytic Drugs," The Pharmacologic Basics of Therapeutics, 7th ed., Gilman et al., eds., Macmillan Publishing Co. (1985).

Mahadoo, "Evidence for a Cellular Pool for Exogenous Heparin" International Symposium on Heparin, Saskatoon, Sask., (1977).

Jaques et al., "Pharmacodynamics and Clinical Effectiveness of Heparin" Seminars in Thrombosis and Hemostasis, 4:298–325 (1978).

Kakkar, "Low Dose Heparin in the Prevention of Venous Thromboembolism," Thrombos. Diathes. Haemorrh., 33:87–96 (1974).

Gallus, "Prevention of Venous Thromboembolism," Seminars in Thrombosis and Hemostatis, 2:232–290 (1976).

EXTRALUMINAL REGULATION OF THE GROWTH AND REPAIR OF TUBULAR STRUCTURES IN VIVO

This invention was funded at least in part by the U.S. Government, and the Government, therefore, has certain rights in this invention.

This is a continuation of application Ser. No. 07/769,162, filed on Sep. 27, 1991, now abandoned, which is a continuation of application Ser. No. 07/436,337, filed Nov. 13, 1989, now abandoned.

BACKGROUND OF THE INVENTION

This invention relates to the general field of regulation of the growth and repair of tubular, or luminal, structures.

Tubular structures within the body (including bronchi of the lung, the entire gastrointestinal tract from the esophagus to the anus, the ureters and urethra of the genitourinary system, the fallopian tubes and vas deferens of the reproductive system, and the blood vessels) are all subject to luminal constriction and obstruction to flow. As a result, tissues and organs downstream of the obstruction are deprived of vital elements and tissues and organs upstream are dammed up with toxic products.

Surgical repair is often indicated in an attempt to relieve these obstructions. However, the repair may be unsuccessful or short-lived due to accelerated obstruction and a recurrence of the events that led to the initial crisis. Overproliferation of smooth muscle cells (SMC) as part of the natural repair process may contribute to luminal occlusion. In the arterial system, for example, restenosis rates of 25 to 35% have been noted within three months following percutaneous balloon angioplasty, and current estimates of the life expectancy of saphenous venin bypass grafts do not exceed 7 years. In the gastrointestinal system, this same phenomenon presents as recurrent bowel obstruction after lysis of adhesions or surgical anastomotic repair, and in the reproductive system as an ineffective surgical repair of the fallopian tubes or vas deferens.

There have been various attempts to limit occlusion. For example, for blood vessels, effort has been directed at various circulating (intravenous) factors such as heparin. Such factors inhibit or stimulate the clotting process and may also affect smooth muscle cell proliferation. Attempt have also been made to control environmental factors such as blood pressure, cholesterol, or smoking (nicotine). As regards lungs, attempts to limit occlusion have been directed at aerosolized factors and modulators of vascular tone (e.g., bronchodialators) and control of mucous formation. Efforts concerning the genitourinary system have focused on maintaining adequate flow, e.g. by controlling pH to enhance the solubility of stone material or by mechanical means such as ultrasound energy to break-up stones or uretal stents.

SUMMARY OF THE INVENTION

In general, one aspect of the invention features a method of regulating repair following injury to luminal tissue that includes administering a modulator of cell or tissue growth at an extraluminal site adjacent the injured tissue. "Regulating repair" is meant to include controlling luminal occlusion (e.g., the reduction or the prevention of formation of such occlusion) and also to include increasing the vascularization of the extraluminal site adjacent the luminal tissue. By luminal tissue is meant the tissue, primarily endothelium, in the lumen of a tubular structure. A modulator is an agent that effects a change in the rate of cell or tissue growth. An extraluminal site is one located outside and adjacent to the injured tubular structure, one example being the adventitia, the layer of loose connective tissue forming the outermost coating of an organ.

Preferred embodiments of the invention include the following features. The invention is particularly appropriate for controlling repair of the vascular system, preferably repair of an artery, and the preferred modulating agent is either anticoagulant or non-anticoagulant heparin. The modulator preferably is delivered to the adventitia adjacent the artery in a polymer matrix (e.g., an ethylene-vinyl acetate copolymer), at a rate of from 1 μg to 100 mg/day, for a period of at least 24 hours. Other sites of injury for which the method is particularly appropriate include the fallopian tubes or the vas deferens of the reproductive system, the ureter or the prostate gland of the genitourinary system, the bowel of the gastrointestinal system, or the trachia or the bronchial tree of the pulmonary system. Other vehicles for administration include aqueous gels, foams, or sprays (e.g. aerosolized).

In another aspect, the invention generally features a method of testing the effectiveness of a modulator in regulating repair following injury to luminal tissue that includes administering the modulator to an extraluminal site adjacent the tissue and determining the extent of regulation of repair following such administration.

Local administration of a modulating agent to an extraluminal site adjacent an injured luminal structure or organ allows for orderly repair of the injured endothelium while reducing detrimental side effects of other forms of administration.

Other features and advantages of the invention will be apparent from the following description of the preferred embodiment thereof, and from the claims.

DESCRIPTION OF THE PREFERRED EMBODIMENT

The method of the invention permits local administration of a modulator of cell or tissue growth to the outside of a tubular (or luminal) physiological structure for the purpose of regulating the repair of that structure following injury, for example, by surgical procedures. Regulation of repair includes direct control of luminal occlusion as well as indirect control by controlling vascularization of the tissue surrounding the lumen. Examples of systems containing such structures and typical surgical procedures where regulating the repair process would be valuable are the vascular system (e.g., vascular anastomses that accompany procedures such as organ transplant, coronary by-pass surgery, systemic arterio-arterio and arterio-venus bypass surgery, and arterio-venus shunts that accompany vascular access for dialysis); the reproductive system (reversal of tubal ligation or vasectomy); genitourinary system (prostate surgery; gastrointestinal system (anastomotic repair of a bowel obstruction); and the pulmonary system (repair or reconstruction of traumatic or surgical injury to trachial or bronchial structures).

A wide range of growth modulating agents are appropriate for use in carrying out the method of the invention including those indicated as affecting angiogenesis, smooth muscle cell proliferation or vascularization. Some examples (as described in more detail below) include heparin, the angiotensin converting enzyme inhibitors (e.g., captopril), angiotensin, angiogenic growth factors (e.g., fibroblast growth factor); immunosupressants (e.g., cyclosporine); and calcium channel inhibitors (e.g., nifedipine).

The modulator may be delivered to the appropriate site outside the tubular structure of interest in a delivery system, e.g., a matrix composed of the modulator in solid form and a polymer, such as an ethylene-vinyl acetate copolymer (described in detail below). The polymer matrix delivery system can be made from any generally inert biocompatible polymer material. The material can be formed in a matrix as described below, or it can be in capsule form or other known controlled release configurations. Desired kinetics for the release of a particular drug can be achieved by known techniques by controlling the matrix fabrication techniques or the nature of the polymer of the delivery system.

A polymer matrix system to deliver the modulating agent is particularly useful when the substance to be delivered is unstable in solution, rapidly degraded, prone to precipitation, or of limited solubility. Alternate delivery systems which may be especially appropriate for modulating agents include bioerodible systems such as polyorthoester systems described in Sparer et al., *J. Controlled Release*: 23–32 (1984); poly (glycolide-CO-DL-lactide) microcapsules disclosed in Lawter et al., *Proc. Int'l. Symp. Control. Rel. Bioact. Mater.* 14: 99–100 (1987); and poly (organophosphazene) bound drugs as disclosed by Neenan and Allcock, Biomaterials 3: 78–80 (1982), and Grolleman et al., *J. of Controlled Release* 3: 143–154 (1986).

A particularly preferred polymer release matrix is the ethylene-vinyl acetate copolymer (EVAc) matrix described in Folkman and Langer U.S. Pat. No. 4,391,797, hereby incorporated by reference.

A particularly preferred cell and tissue growth modulating agent is heparin, an α,β-glucosidically linked, highly sulfated copolymer of uronic acid and glucosamine. Preparations are polydisperse with a molecular weight range of from 5,000–40,000 daltons. The precise composition of commercial heparin and the precise degree of antiproliferative activity vary depending on the source and method of purification. By the term "heparin," we mean to include all forms of heparin and all fragments of heparin having an antiproliferative effect, e.g., both anticoagulant heparin and non-anticoagulant heparin (e.g., heparin that is identified by its failure to bind to an anti-thrombin III affinity column) have antiproliferative activity. Other well known methods of preparing non-anticoagulent heparin include modification of native heparin by periodate oxidation or by enzymatic degradation, and de novo synthesis.

To establish loading of a matrix, drug release in vivo from the matrix (e.g. an EVAc matrix) is assumed to mirror release in vitro (Brown et al., *J. Pharm. Sci.* 72:1181–1185 (1983)). The maximum number of units of modulator to be applied directly to the extraluminal tissue (e.g., an arterial wall) can be estimated by using in vitro release data. Animal models such as those described below provide a dose response curve. To scale up from animal to human delivery, e.g., in human arteries, one considers only the difference in luminal diameter (e.g., scaling up from rat to human vessel diameter involves a factor of approximately four to ten-fold). Because achieving systemic effects is not desired, body weight does not enter into the calculation.

At the time of surgical intervention of a typical surgical procedure, the polymer matrix embedded with the modulator is placed at an extraluminal site (e.g., in the adventitia) adjacent the injured lumen (e.g., artery) and the adjacent muscles and facia are sutured closed to insure immobilization of the matrix. During recovery of the patient, fluid is absorbed by the matrix and solubilizes the modulator, which then diffuses in solution through the channels of the matrix and out into the adventitia. Positioning of the matrix in the adventitia assures that heparin delivery takes place at the exterior surface of the blood vessel wall, at the site of injury.

The following examples of specific procedures, modulators and delivery systems used in animal models are provided to illustrate and not to limit the invention.

EXAMPLE 1

Heparin, particularly non-anticoagulent heparin, can be administered to an artery from an EVAc slow release matrix according to the following example.

An EVAc matrix loaded with 0.1–1000 mg (most preferably 0.5–500 mg) non-anticoagulent heparin is prepared as described below. As part of the surgical procedure, (e.g. coronary by-pass or coronary valve replacement) the matrix is sutured in the adventitia adjacent the artery. The adjacent muscles and facia are sutured closed to immobilize the matrix adjacent the arterial repair. The heparin is released at a rate of 1 µg-100 mg/day, for more than one (preferably more than three, and most preferably more than seven) days.

EXAMPLE 2

Anti-coagulant (AC) heparin (Choay Heparin 1453, m.w. 12,000–18,000 dalton, U.S.P. 160 U/mg, in vitro antiproliferative activity 80% (as described by Casteliot et al. (1987) *Seminars in Thrombosis and Hemostasis* 13:489–503) or non-anti-coagulant (NAC) heparin (Choay heparin 1772, m.w. 5000–8000 dalton, U.S.P. 10 U/mg, in vitro antiproliferative activity 80%), Choay Institute, Paris, France, were embedded in polymer matrices using a solvent casting technique as described in Langer et al., *Methods in Enzymol.* 112:399–423 (1985). First, ethylene-vinyl acetate copolymer (ELVAX-40P, 40% vinyl acetate, E. I. DuPont, Wilm., Del. or U.S.I. of Cincinnati, Ohio) was dissolved in methylene chloride to a concentration of 10% (w/v). Dry powdered heparin was then sieved to particle sizes less than 180 microns and added to the EVAc solution. If the heparin aggregated, the drug was dissolved in normal saline, lyophylized to a powder, pulverized with mortar and pestle in a humidity controlled box and then sieved and added to the dissolved EVAc. The drug-polymer suspension was vortexed, let stand for 15 seconds to allow air bubbles to settle out and then poured into glass molds that had been precooled on dry ice. At these temperatures, the heparin was immediately frozen in place so as to be uniformly distributed through the matrix and not settle on the bottom. The resultant matrix was a homogeneous dispersion of heparin within EVAc. Once hardened, the matrices were removed from their glass molds, placed in a −20° C. freezer for two days and then under vacuum (600 mtorr) for another two days.

For use, smaller pellets were cut from the larger slabs to specific sizes and weights, and a coating was applied by placing a 20 gauge intravenous needle one cm into the center of the face of the matrix pellet and then immersing the pellet in a solution of 10% EVAc dissolved in methylene chloride for 5 seconds. As the pellets were withdrawn from the solution, they were spun slowly for a minute to allow for uniform coating. This entire process was repeated twice more. The matrices were left on the needles and placed in a chemical fume hood to allow for further solvent evaporation. After 12 hours, the extraneous polymer material that had migrated up the needle was removed by spinning a tweezers around the base of the needle as it was withdrawn from the matrix pellets. This insured that the extra polymer material did not collapse over the hole and that the hole remained open. Matrices were stored in a dessicator where solvent evaporation continued to completion.

Male Sprague-Dawley rats (300–500 gm, Charles River Breeding Laboratories, Wilmington, Mass.) were anesthetized with sodium nembutol 0.5 mg/gm body weight, and supplemental anesthesia was maintained with ether inhalation. A midline incision was made from the mandible to the mid-sternum. The carotid artery was exposed along the length of the bifurcation with blunt dissection, and the external carotid artery was isolated and ligated in its cephalad portion. A 2 French Fogarty balloon catheter (American Edwards Laboratories, Santa Ana, Calif.) was introduced into the arteriotomy of the external carotid artery and passed in its inflated state over the endothelium of the common carotid artery three times. The catheter was then deflated and removed from the external carotid artery, which was then ligated. In different groups of animals, EVAc matrices containing no drug, AC heparin or NAC heparin were placed adjacent to the injured artery. The adjacent muscles and fascia were sutured closed with 4-0 nylon suture to insure immobilization of the pellet. The midline incision was closed with the same suture and animals observed in separate cages during recovery. As a control, To demonstrate that the effect at issue is specific for adventitial or extraluminal delivery, EVAc matricies were placed in a subcutaneous pocket over the animal's dorsal neck region. In other animals, an osmotic infusion pump (ALZA Corporation, Palo Alto, Calif.) provided continuous iv administration of these same agents. The pump was placed in a pocket made in the neck of the rat, and a silastic catheter extended from the pump to the right internal jugular vein. AC and NAC heparins were mixed in lactated Ringer's solution and delivered at 0.3 mg per kilogram of body weight per hour. Control animals received lactated Ringer's infusion. The overall doses of the drugs administered are displayed in Table I.

TABLE I

| | HEPARIN DOSAGE mg (over 14 days) | | |
|---|---|---|---|
| | INTRA- | MATRICES | |
| | VENOUS | CAROTID | DORSAL |
| NAC | (5) 25.9–43.3* | (10) 19.5 ± 1.9 | (5) 18.5 ± 2.9 |
| AC | (5) 25.9–43.3* | (8) 8.1 ± 1.9 | (4) 7.1 ± 0.2 |

*set to 0.3 mg/kg/hr and dictated by the size of the animal
numbers in parentheses represent the number of animals in each group As an indication of anti-coagulation activity, activated partial thromboplastin times (aPTT) were determined within the first 24–36 hours after the procedure and at day 14. To observe the percent of luminal occlusion, animals were euthanized while undergoing intravascular fixation perfusion using methods described in A. W. Clowes et al., *Lab. Invest.* 49:327 et seq. (1983). Photomicrographs of all arterial sections were obtained, and the percent of luminal occlusion was calculated for each arterial segment using computerized digital planimetry. Specifically, the natural lumen boundary is apparent by photomicroscopy. The boundary is extended inwardly by inclusions. Digital planimetry is used to provide a measure of the cross-sectional area of the natural lumen boundary, divided into the area of the inclusion, yielding percent occlusion.

Anti-coagulation activity as given by the aPTT (Table II) and extent of luminal occlusion (Table III), for each animal group, are detailed below.

TABLE II

| | aPTT (sec) | | |
|---|---|---|---|
| | INTRA- | MATRICES | |
| | VENOUS | CAROTID | DORSAL |
| CONTROL | (6) 16.2 ± 0.1 | (8) 16.5 ± 0.4 | |
| NAC | (5) 18.4 ± 0.6 | (10) 15.0 ± 0.4 | (5) 17.5 ± 0.5 |
| AC | (5) 40.0 ± 11.8* | (8) 15.3 ± 0.1 | (4) 17.0 ± 1.0 | numbers in parentheses represent the number of ± animals in each group
statistical significance compared with corresponding controls: * $p < 0.0005$

TABLE III

| | LUMINAL OCCLUSION (%) | | |
|---|---|---|---|
| | INTRA- | MATRICES | |
| | VENOUS | CAROTID | DORSAL |
| CONTROL | (6) 52.2 ± 4.2 | (8) 55.9 ± 4.3 | |
| NAC | (5) 46.4 ± 3.9 | (10) 17.7 ± 3.78@ | (5) 45.0 ± 2.0 |
| AC | (5) 16.8 ± 4.3** | (8) 9.4 ± 2.6* | (4) 28.0 ± 2.6 | numbers in parentheses represent the number of animals in each group
statistical significance compared with corresponding controls:
*$p < 0.0005$, ** $p < 0.0003$, @ $p < 0.0001$ Referring to Table II, only the intravenous administration of AC heparin produced systemic anti-coagulation. Neither the local matrix delivery of either heparin, in subcutaneous or adventitial positions, nor the intravenous infusion of NAC heparin had any discernable effect on clotting function. None of the animals in any groups suffered from excessive bleeding. Referring to Table III, intravenous AC heparin infusion reduced luminal occlusion 68%, from a control value of 52.2 to 16.8%. NAC heparin delivered in the same fashion achieved only an 11% reduction (no statistical difference in comparison to control). Subcutaneous matrix delivery of NAC heparin also showed no significant difference in luminal occlusion, but similar delivery of AC heparin reduced occlusion by 52%. The largest effect on luminal occlusion was observed with adventitial delivery. Occlusion was reduced from 55.9% to 9.4% (83% reduction) in animals with AC heparin matrices, and to 17.7% (68% reduction) in animals with NAC heparin matrices.

EXAMPLE 3

To generate a dose response curve for NAC heparin, twelve rats were implanted with NAC heparin-bearing matrices of different net weights so as to deliver different dosages of heparin over the 14 day period. As the dose of the NAC heparin was increased, the effect on SMC proliferation rose, such that at the highest dose tested, NAC heparin inhibited SMC proliferation to an equal extent as AC heparin, at five times the equivalent dose. A dose response experiment was not performed for AC heparin as the amount of heparin delivered in the uniform dose study was already low and had achieved over 80% inhibition of SMC proliferation.

At a rate of about 0.8 mg/day for in vitro release, the maximum amount of heparin human arteries would be exposed to would be no higher than 20–50 units/hour, and systemic levels would be undetectable. This is in marked contrast to the 1000–1500 units/hour of i.v. infusion currently used in clinical practice for systemic anticoagulation.

In vitro release kinetics were defined for five flat slab (15, 30 or 50% heparin:EVAc w/w), and for five slabs coated with plain EVAc (at 15 or 30% concentration) with a hole drilled into one face. Uncoated matrices exhibited first order release kinetics with the bulk of the drug eliminated in the first 24 to 48 hours. At higher matrix concentrations, heparin was released more rapidly and to a greater extent. When a coating was applied and release constrained to emanate from a hole drilled into the coated polymer face, the initial burst of release was eliminated but overall amount delivered sustained.

EXAMPLE 4

Angiotensin II (AII) has been demonstrated to have both inhibitory and stimulatory effects on SMCs in tissue culture and has also been demonstrated to induce blood vessel growth in avascular structures such as the the rabbit cornea, independent of its hemodynamic effects. Matrices of ethylene-vinyl acetate copolymer were embedded with AII and sustained first order release demonstrated for more than one month. As the drug is potent in ng quantities, the EVAc matrix drug embedding technique was modified to include bovine serum albumin (BSA) as a carrier compound. When dry powdered AII was mixed with dry powdered BSA in a 1 to 500 ratio and then embedded within a EVAc matrix, the rate of BSA release dictated the rate of AII release. When this system was then placed in the balloon injury model described above, the vascular occlusion was noted and the number of blood vessels surrounding the implant counted and compared to control.

DOSE: 17 µg over the course of 14 days
LUMINAL OCCLUSION: 22.5–64%
INHIBITION COMPARED TO CONTROL: 0–62.6%
NUMBER OF VESSELS SURROUNDING AII IMPLANT: 27
NUMBER OF VESSELS SURROUNDING CONTROL IMPLANT: 6

Angiotensin II was able to induce a marked vascular response regardless of its ability to control SMC proliferation.

EXAMPLE 5

Fibroblast growth factor (FGF) in culture is a mitogen for a number of cell types and a potent angiogenesis factor in vivo that has no apparent effect on blood pressure. As FGF activity is lost if the factor is embedded in standard controlled release devices, an alternative method was used, taking of advantage the inherent ability of FGF to adhere to heparin.

FGF (Takeda Industries, Japan) was bound to heparin sepharose beads to stabilize the factor and to provide a solid carrier for minute quantities of the liquid growth factor. Aliquots of FGF were mixed with 2 ml of $I^{125}$FGF (1.2 mg/ml) and then incubated for 1 hour with the heparin sepharose beads. Subsequent release of FGF from the beads was followed in 0.15M NaCl buffer. Microspheres containing FGF were constructed by dropping a mixture of sodium alginate (1%) with heparin sepharose bead-bound FGF through a glass Pasteur pipette into a hardening solution of calcium chloride (1.5 weight %). Release kinetics were determined for microcapsules containing 6 ml of FGF and 2 ml of $I^{125}$FGF bound to 125 mg of the heparin sepharose beads in 500 ml of 0.15M NaCl. Heparin sepharose bead-laden FGF was incorporated within alginate microcapsules with 74% efficiency, and release of the FGF over time was retarded and prolonged in comparison to release from the unencapsulated beads. Bioactivity was retained by 87.6±12% of the factor preparation. Microspheres prepared as above were placed adjacent to noninjured and balloon endothelialized carotid arteries. In both blood vessels a significant increase in local vascularity was noted.

In addition to the examples described above, the method can be used in a laboratory setting to test the luminal repair-enhancing effect of a variety of potentially potent cell or tissue growth modulators previously discarded as ineffective because they do not act systemically, do not act in a similar fashion over a range of dosages, are degraded before they achieve their effects if applied systemically, or have side effects when delivered systemically.

Other embodiments are within the following claims.

We claim:

1. A method of regulating repair of a patient's blood vessel wall following surgical anastomosis at a location along said blood vessel, said method comprising, administering outside said blood vessel at said location, a biocompatible polymer based heparin releasing system, said biocompatible polymer based heparin releasing system releasing said heparin into the wall of said vessel at said location, said administration taking place over a period of at least 24 hours and being characterized by a rate of less than 100 mg/day and dosage selected to be:
   a) high enough to control proliferation of smooth muscle cells in said vessel wall at said location; and
   b) low enough to avoid transport of said heparin through said vessel wall to establish a heparin level in the blood system equivalent to an anticoagulant heparin level that would have a discernable effect on clotting function as measured by activated prothrombin time (aPTT).

2. The method of claim 1 wherein said heparin is non-anticoagulant heparin.

3. The method of claim 1 wherein said heparin is anticoagulant heparin.

4. The method of claim 1 wherein said blood vessel is an artery.

5. A method of regulating repair of tissue at a location in a patient's blood vessel wall comprising administering outside said blood vessel at said location, a biocompatible polymer based heparin releasing system, said biocompatible polymer based heparin releasing system releasing said heparin into the wall of said vessel at said location, said administration taking place over a period of at least 24 hours and being characterized by a rate and dosage selected to be:
   a) high enough to control proliferation of smooth muscle cells in said vessel wall at said location; and
   b) low enough to avoid transport of said heparin through said vessel wall to establish a heparin level in the blood system equivalent to an anticoagulant heparin level that would have a discernable effect on clotting function as measured by activated prothrombin time (aPTT).

6. The method of claim 5 wherein said heparin is non-anticoagulant heparin.

7. The method of claim 5 wherein said heparin is anticoagulant heparin.

8. The method of claim 5 wherein said blood vessel is an artery.

9. The method of claim 8 wherein said biocompatible polymer based heparin releasing system comprises an aqueous gel or foam.

10. The method of claim 5 comprising treating said tissue to promote healing after surgical repair of said vessel at said location.

* * * * *

UNITED STATES PATENT AND TRADEMARK OFFICE
CERTIFICATE OF CORRECTION

PATENT NO. : 5,455,039

DATED : October 3, 1995

INVENTOR(S) : E. R. Elelman et al

It is certified that error appears in the above-identified patent and that said Letters Patent is hereby corrected as shown below:

Cover page col. 1, under [56] References Cited, OTHER PUBLICATIONS, lines 8-17, are duplicate citations.

Cover page, col. 1, under [56] References Cited, OTHER PUBLICATIONS, line 19, "Costellot" should be --Castellot--; after "et al", insert --.--.

Cover page, col. 1, under [56] References Cited, OTHER PUBLICATIONS, line 21, after "et al", insert --.--.

Cover page, col. 1, under [56] References Cited, OTHER PUBLICATIONS, line 19, after "Jr.,", insert --et al.,--.

Cover page, col. 2, under [56] References Cited, OTHER PUBLICATIONS, line 25, after "II", delete the quotations.

Cover page, col. 2, under [56] References Cited, OTHER PUBLICATIONS, line 26, delete the quotations before "Evidence" and after "Group," ".

UNITED STATES PATENT AND TRADEMARK OFFICE
CERTIFICATE OF CORRECTION

PATENT NO. : 5,455,039

DATED : October 3, 1995

INVENTOR(S) : E.R. Edelman et al.

It is certified that error appears in the above-identified patent and that said Letters Patent is hereby corrected as shown below:

Col. 2, line 55, after "surgery", insert --)--.

Col. 2, line 67, "immunosupressants" should be --immunosuppressants--.

Col. 3, line 20, after "Release", insert --1--.

Col. 4, line 28, "Casteliot" should be --Castellot--.

Col. 5, line 24, "To" should be --to--.

Col. 8, line 58, after "rate", insert --of less than 100 mg/day--.

Signed and Sealed this

Seventh Day of October, 1997

Attest:

BRUCE LEHMAN

Attesting Officer

Commissioner of Patents and Trademarks